(12) United States Patent
Gehner et al.

(10) Patent No.: US 8,033,392 B1
(45) Date of Patent: Oct. 11, 2011

(54) MOUTH GUARD HOLDING ASSEMBLY AND METHOD

(76) Inventors: Todd Gehner, Sioux City, IA (US);
Christine Gehner, Sioux City, IA (US)

( * ) Notice: Subject to any disclaimer, the term of this patent is extended or adjusted under 35 U.S.C. 154(b) by 0 days.

(21) Appl. No.: 12/648,403

(22) Filed: Dec. 29, 2009

(51) Int. Cl.
*B65D 81/24* (2006.01)
(52) U.S. Cl. .............................. 206/207; 206/83; 206/37
(58) Field of Classification Search .................. 206/279, 206/288, 289, 37, 290, 83, 63.5; 215/399
See application file for complete search history.

(56) References Cited

U.S. PATENT DOCUMENTS

| | | | |
|---|---|---|---|
| 1,488,456 A | | 3/1924 | Harper |
| 2,163,862 A | | 6/1939 | Wing |
| 2,541,595 A | * | 2/1951 | Marshall et al. .............. 206/205 |
| 2,565,899 A | | 8/1951 | Wilcox |
| 2,964,047 A | * | 12/1960 | Jackson et al. ................. 134/183 |
| 3,066,687 A | | 12/1962 | Rohmann |
| 3,894,551 A | | 7/1975 | Stohlman |
| 4,802,853 A | * | 2/1989 | Krasner ........................ 433/215 |
| 4,966,319 A | * | 10/1990 | Fleming ........................ 224/615 |
| 5,000,209 A | | 3/1991 | Mann |
| 5,201,411 A | * | 4/1993 | Elkins et al. .................... 206/83 |
| 5,314,543 A | | 5/1994 | Elkins et al. |
| 5,402,810 A | * | 4/1995 | Donley ......................... 134/135 |
| 6,213,777 B1 | | 4/2001 | Seitzinger |
| 6,343,612 B1 | * | 2/2002 | Dahl ............................. 134/117 |
| 6,499,494 B2 | * | 12/2002 | Berghash et al. ............. 134/135 |
| D482,165 S | | 11/2003 | Kay |
| 2004/0099562 A1 | * | 5/2004 | Vazquez ....................... 206/461 |
| 2006/0076250 A1 | * | 4/2006 | Kwasney ........................ 206/83 |
| 2007/0084749 A1 | * | 4/2007 | Demelo et al. ................ 206/569 |

* cited by examiner

*Primary Examiner* — Mickey Yu
*Assistant Examiner* — Rafael Ortiz

(57) ABSTRACT

A mouth guard holding assembly includes a housing assembly with a container having a bottom wall and a perimeter wall. An intermediate wall is attached to and is coextensive with an inner surface of the perimeter wall. The intermediate wall has an outer edge and a central area. The intermediate wall is contoured downwardly toward the bottom wall from the outer edge to the central area. The intermediate wall has a plurality of drainage apertures extending therethrough. A cover is removably attached to the perimeter wall and closes the access opening. A cleansing solution is positionable in the housing and a mouth guard is positionable on the intermediate wall so that the cleansing solution cleans the mouth guard when the housing is titled and the cleansing solution enters a space between the intermediate wall and the cover through the apertures.

8 Claims, 4 Drawing Sheets

MOUTH GUARD HOLDING ASSEMBLY AND METHOD

BACKGROUND OF THE DISCLOSURE

Field of the Disclosure

The disclosure relates to mouth guard holding devices and more particularly pertains to a new mouth guard holding device for cleaning a mouth guard between uses and to prevent its contact with a player's stored sporting equipment.

SUMMARY OF THE DISCLOSURE

An embodiment of the disclosure meets the needs presented above by generally comprising a housing assembly with a container having a bottom wall and a perimeter wall that is attached to and extends upwardly from the bottom wall. The perimeter wall has a free edge defining an access opening into the container. An intermediate wall is attached to and is coextensive with an inner surface of the perimeter wall. The intermediate wall has an outer edge and a central area. The intermediate wall is contoured downwardly toward the bottom wall from the outer edge to the central area. The intermediate wall has a plurality of drainage apertures extending therethrough. A cover is removably attached to the perimeter wall and closes the access opening. A cleansing solution is positionable in the housing and a mouth guard is positionable on the intermediate wall so that the cleansing solution cleans the mouth guard when the housing is titled and the cleansing solution enters a space between the intermediate wall and the cover through the apertures.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
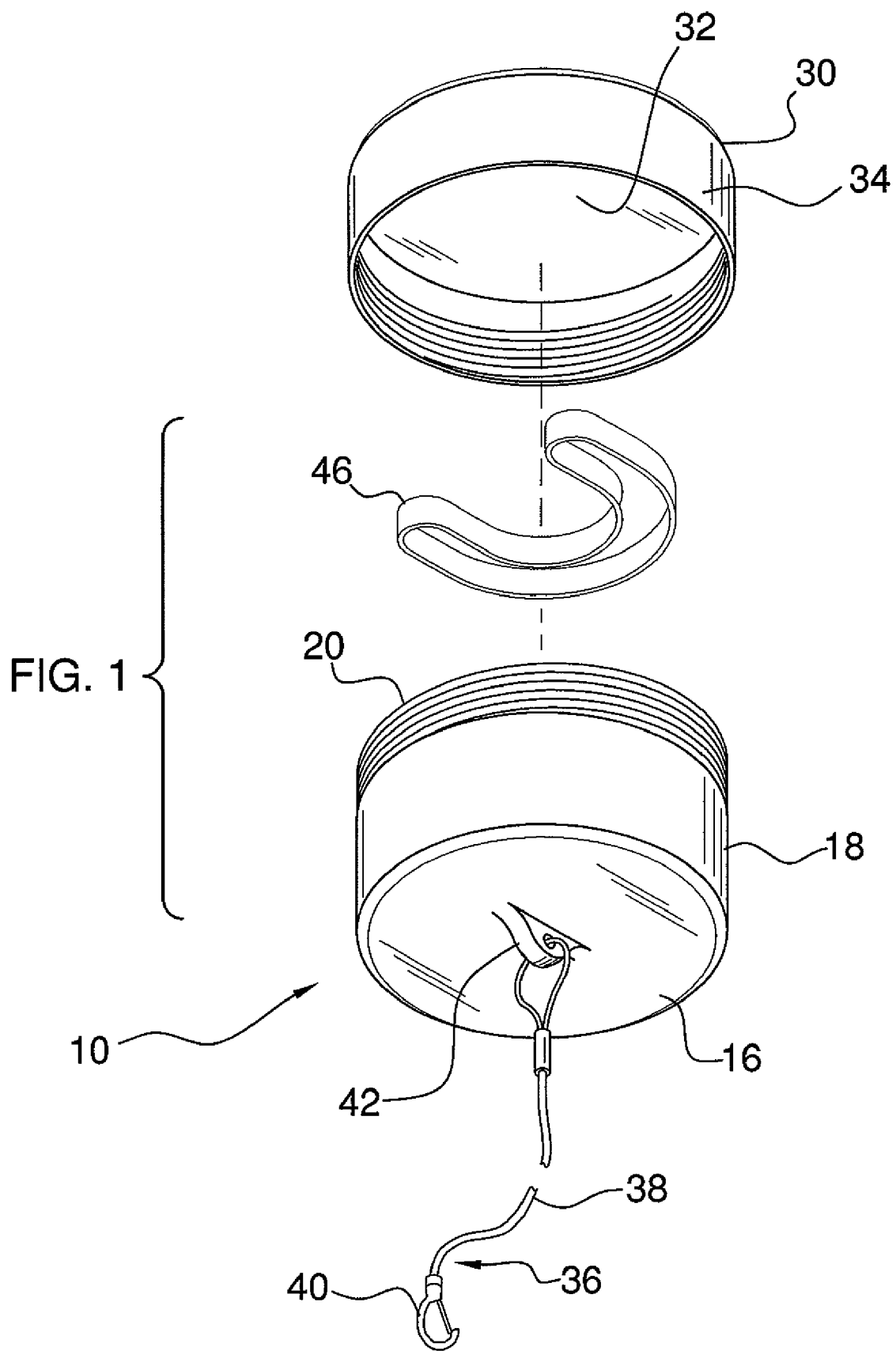
FIG. 1 is a bottom perspective view of a mouth guard holding assembly and method according to an embodiment of the disclosure.
Figure 2:
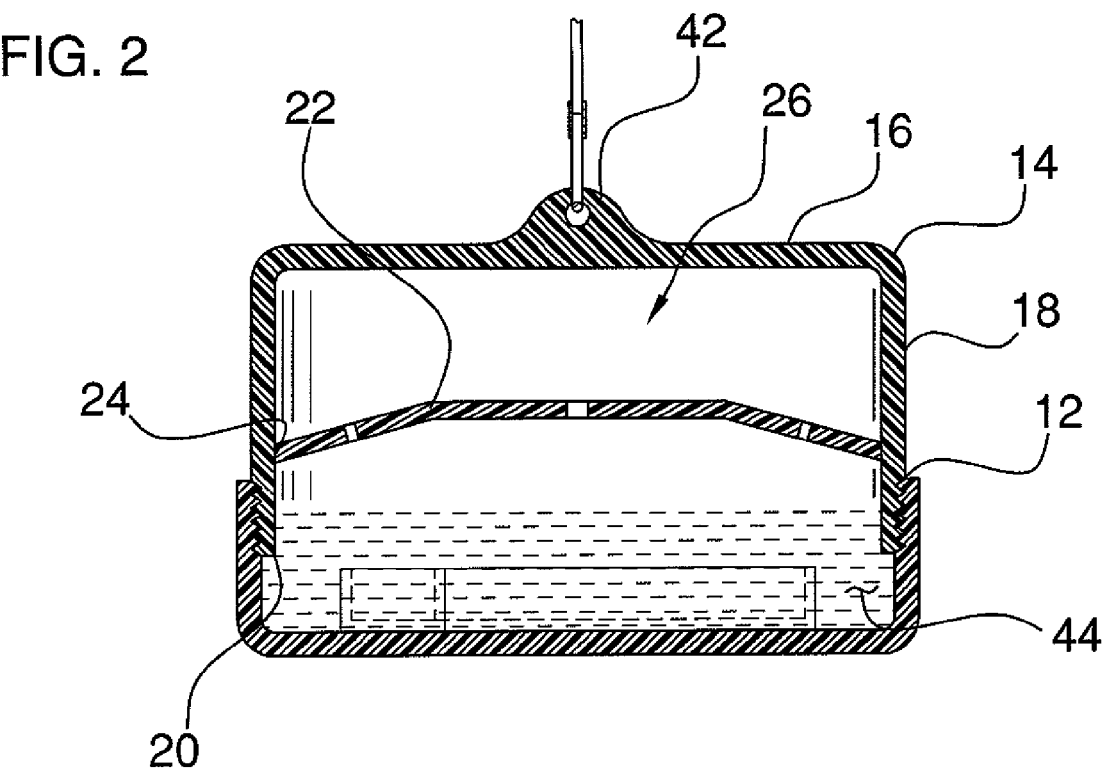
FIG. 2 is a side cross-sectional view of an embodiment of the disclosure.
Figure 3:
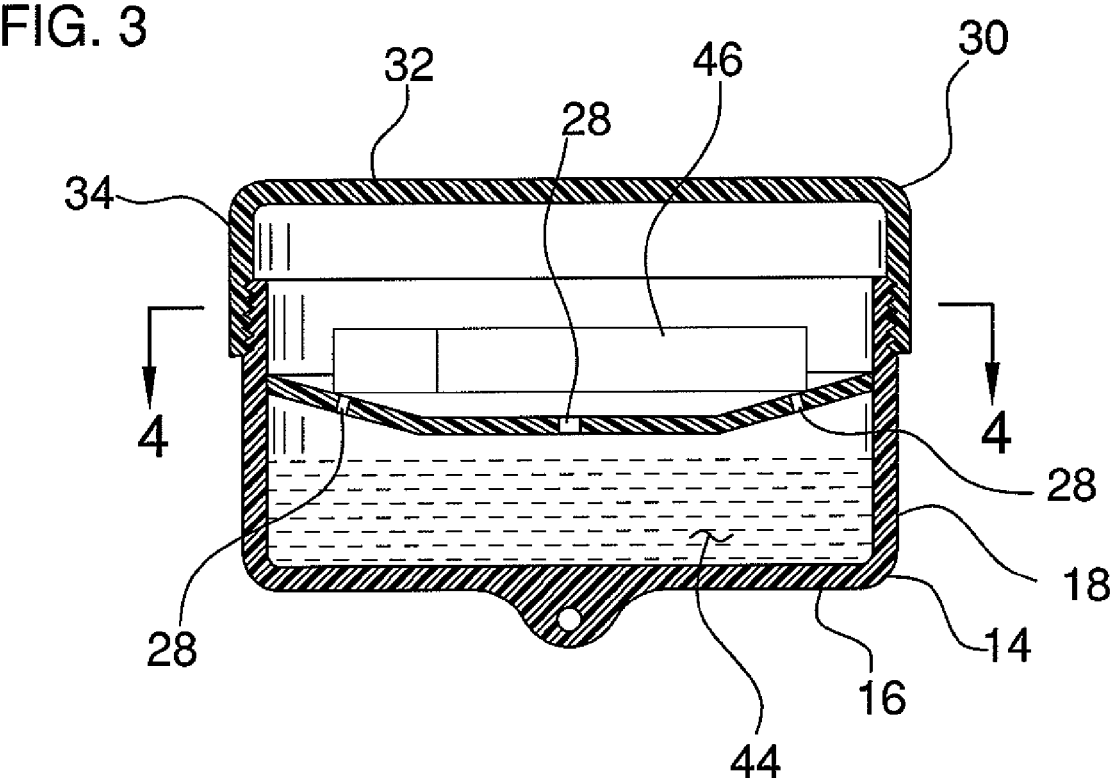
FIG. 3 is a side view of an embodiment of the disclosure.
Figure 4:
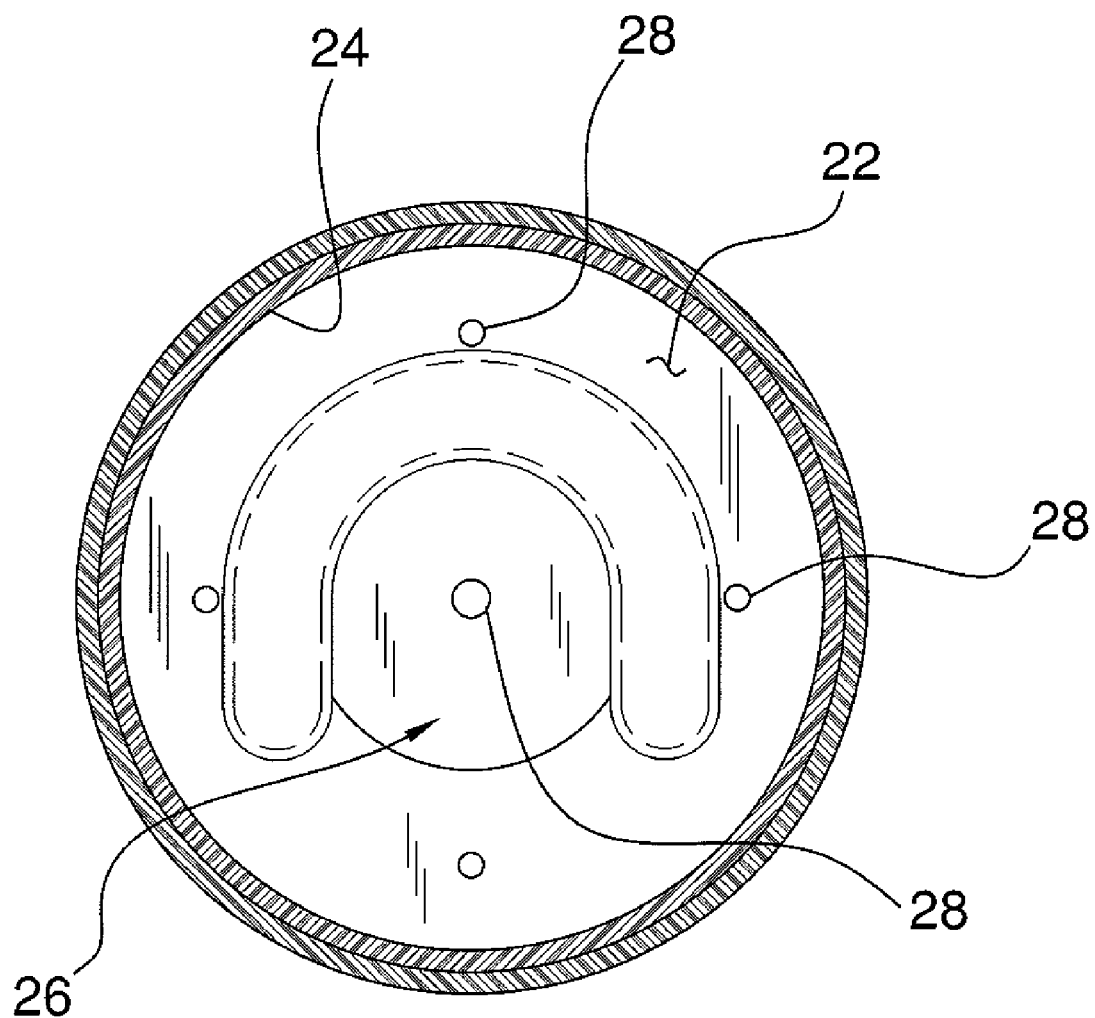
FIG. 4 is a cross-sectional view of an embodiment of the disclosure taken along line 4-4 of FIG. 3.
Figure 5:
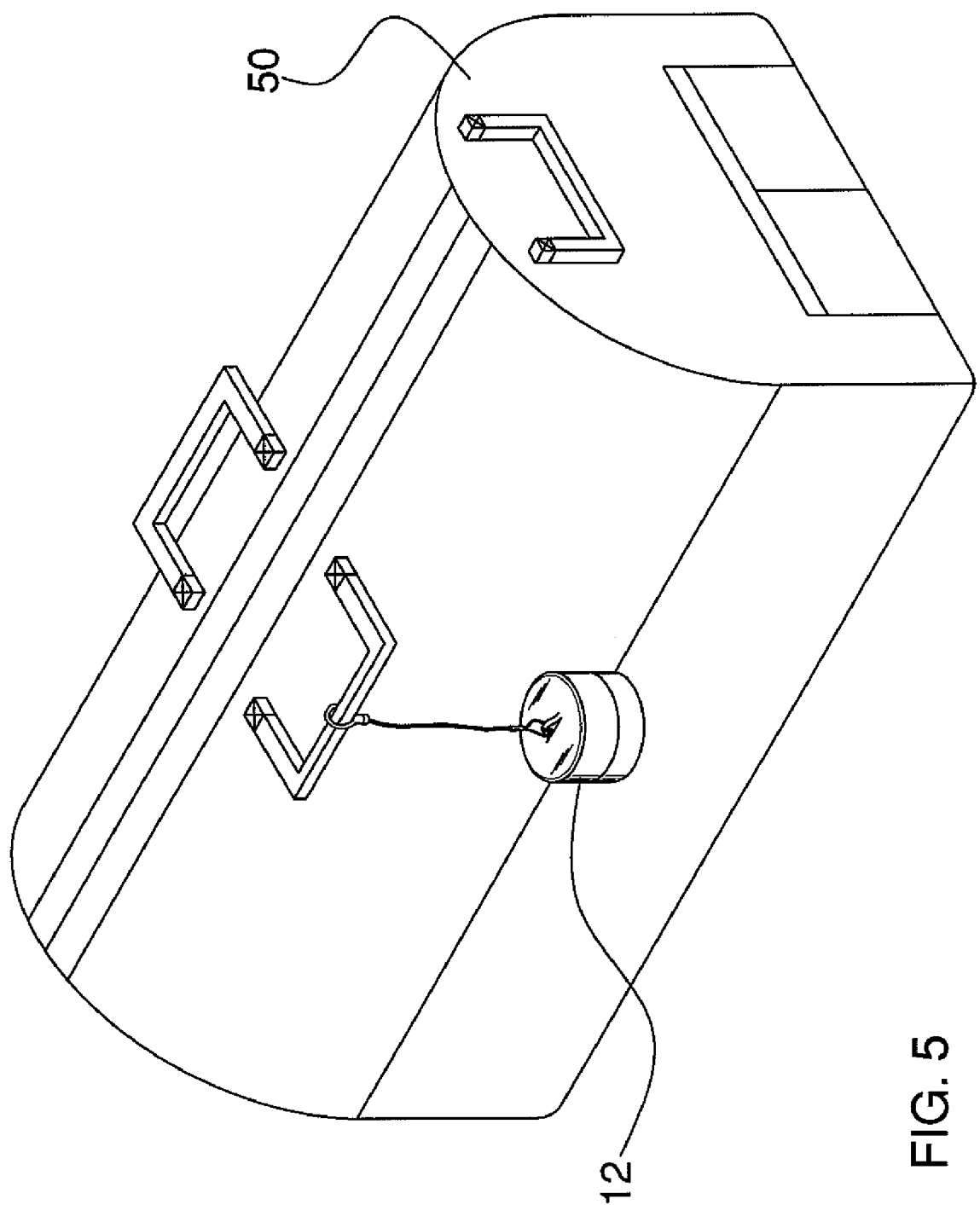
FIG. 5 is a perspective in-use view of an embodiment of the disclosure.

With reference now to the drawings, and in particular to FIGS. 1 through 5 thereof, a new mouth guard holding device embodying the principles and concepts of an embodiment of the disclosure and generally designated by the reference numeral 10 will be described.

As best illustrated in FIGS. 1 through 5, the mouth guard holding assembly 10 and method generally comprises a housing assembly 12 that includes a container 14 with a bottom wall 16 and a perimeter wall 18 attached to and extending upwardly from the bottom wall 16. The perimeter wall 18 has a free edge 20 defining an access opening into the container 12. The bottom wall 16 has a circular shape and the perimeter wall 18 has a cylindrical shape. An intermediate wall 22 is attached to and is coextensive with an inner surface of the perimeter wall 18 to form a sealed barrier between the bottom wall 16 and the free edge 20. The intermediate wall 22 has an outer edge 24 and a central area 26 and is contoured downwardly toward the bottom wall 16 from the outer edge 24 to the central area 26. This causes any solution on the intermediate wall 22 to drain toward the central area 26. The intermediate wall 22 has a plurality of drainage apertures 28 extending therethrough. The drainage apertures 28 are spaced from the outer edge 24 and from the perimeter wall 18. This positioning prevents fluids, between the bottom 16 and intermediate 22 walls, to flow outwardly of the apertures 28 when the container 14 is only slightly deviated from an upright position. The intermediate wall 22 is spaced from the free edge 20.

The housing assembly 12 also includes a cover 30 that is removably attached to the perimeter wall 18 and closes the access opening formed by the free edge 20. The cover 30 is threadably coupled to the container 14 and forms a seal with the perimeter wall 18 to inhibit leakage of solution outwardly of the housing assembly 12 when the access opening is closed. While a threaded coupling means is being utilized, a snap type closure may also be used. The cover 30 includes a top wall 32 and a peripheral wall 34 that is attached to and extends downwardly from the top wall 32.

A coupler 36 is attached to the housing assembly 12 to allow the housing assembly 12 to be securable to a sports bag 50 such as used by hockey players. The coupler 36 may include a tether 38, a clip 40, a combination of the two or any other suitable connecting means. The coupler 36 may be attached to an anchor member 42 attached to the housing assembly 12 and positioned on the bottom wall 16 to encourage the housing assembly 12 to enter an upside down configuration when attached the sports bag 50.

In use, a cleansing and disinfecting solution 44 is positionable in the housing assembly 12 and a mouth guard 46 is positionable on the intermediate wall 22 so that the cleansing solution 44 cleans the mouth guard 46 when the housing assembly 12 is titled and the cleansing solution 44 enters a space between the intermediate wall 22 and the cover 30 through the apertures 28. The housing assembly 12 may be positioned within the sports bag 50 or attached to it with the coupler 36. When the user of the holding assembly 10 wishes to access the mouth guard 46, the solution 44 is allowed to drain through the apertures 28 so that the solution 44 is not spilled outwardly when the cover 30 is removed. The holding assembly 10 allows athletes to use the same mouth guard over a longer period of time without concern of germs and viruses being carried by the mouth guard 46 and prevents the month guard 46 from contacting other articles within a sports bag 50.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

We claim:

1. A method of disinfecting a mouth guard, said method including the steps of:
   positioning a mouth guard in a housing assembly, said housing assembly including;
      a container having a bottom wall and a perimeter wall being attached to and extending upwardly from said bottom wall, said perimeter wall having a free edge defining an access opening into said container, said bottom wall having a circular shape and said perimeter wall having a cylindrical shape;
      an intermediate wall being attached to and being coextensive with an inner surface of said perimeter wall, said mouth guard being positioned on said intermediate wall, said intermediate wall having an outer edge and a central area, said intermediate wall being contoured downwardly toward said bottom wall from said outer edge to said central area, said intermediate wall having a plurality of drainage apertures extending therethrough, said drainage apertures being spaced from said outer edge and from said perimeter wall, said intermediate wall being spaced from said free edge;
      a cover being removably attached to said perimeter wall and closing said access opening, said cover being threadably coupled to said container and forming a seal with said perimeter wall to inhibit leakage of solution outwardly of said container when said access opening is closed, said cover including a top wall and a peripheral wall being attached to and extending downwardly from said top wall;
   positioning a cleansing and disinfecting solution in said housing assembly so that the solution is below said intermediate wall when said container is upright;
   releasably securing said housing to a sports bag with a coupler attached to said housing assembly; and
   cleaning said mouth guard with the solution by tilting said housing assembly to allow the solution to enter a space between the said intermediate wall and said cover through said apertures.

2. The method according to claim 1, wherein the step of positioning said mouth guard in said housing further includes the step of said intermediate wall retaining a contoured shape extending toward said bottom wall when said housing is inverted and said bottom wall is positioned over said intermediate wall.

3. A method of disinfecting a mouth guard, said method including the steps of:
   positioning a mouth guard in a housing assembly, said housing assembly including;
      a container having a bottom wall and a perimeter wall being attached to and extending upwardly from said bottom wall, said perimeter wall having a free edge defining an access opening into said container;
      an intermediate wall being attached to and being coextensive with an inner surface of said perimeter wall, said intermediate wall having an outer edge and a central area, said intermediate wall being contoured downwardly toward said bottom wall from said outer edge to said central area, said intermediate wall having a plurality of drainage apertures extending therethrough;
      a cover being removably attached to said perimeter wall and closing said access opening; and
   positioning a cleansing and disinfecting solution in said housing assembly so that the solution is below said intermediate wall when said container is upright;
   releasably securing said housing to a sports bag with a coupler attached to said housing assembly; and
   cleaning said mouth guard with the solution by tilting said housing assembly to allow the solution to enter a space between the said intermediate wall and said cover through said apertures.

4. The method according to claim 3, wherein the step of said apertures having said drainage apertures further includes said drainage apertures being spaced from said outer edge and from said perimeter wall to retain said solution between said bottom wall and said intermediate wall when said housing is upright.

5. The method according to claim 3, further including the steps of providing a coupler being attached to said housing assembly and attaching said housing assembly to a sports bag with said coupler.

6. The method according to claim 3, wherein the step of positioning said mouth guard in said housing further includes the step of said intermediate wall retaining a contoured shape extending toward said bottom wall when said housing is inverted and said bottom wall is positioned over said intermediate wall.

7. The method according to claim 4, wherein the step of said housing includes said intermediate wall further includes said intermediate wall being spaced from said free edge.

8. The method according to claim 4, further including the steps of threadably coupling said cover to said container and forming a seal with said perimeter wall to inhibit leakage of solution outwardly of said container when said access opening is closed.

* * * * *